US005578039A

United States Patent [19]
Vendrely et al.

[11] Patent Number: 5,578,039
[45] Date of Patent: Nov. 26, 1996

[54] TIBIAL RESECTION INSTRUMENTATION AND SURGICAL METHOD

[75] Inventors: Tim Vendrely, Memphis, Tenn.; Leo A. Whiteside, Bridgeton, Mo.; Thomas A. T. Carls, Memphis, Tenn.; John Steele, Aurora, Colo.; Chris E. Johnson, Memphis, Tenn.

[73] Assignee: Smith & Nephew Richards Inc., Memphis, Tenn.

[21] Appl. No.: 388,983

[22] Filed: Feb. 15, 1995

[51] Int. Cl.⁶ ....................................................... A61B 17/00
[52] U.S. Cl. .............................. 606/88; 128/898; 606/79; 606/82; 606/86
[58] Field of Search ................................... 606/80, 82, 86, 606/87, 88, 96, 102

[56] References Cited

U.S. PATENT DOCUMENTS

| | | | |
|---|---|---|---|
| 4,016,606 | 4/1977 | Murray et al. | 3/1.911 |
| 4,601,289 | 7/1986 | Chiarizzio et al. | 128/305 |
| 4,938,769 | 7/1990 | Shaw | 623/20 |
| 5,080,675 | 1/1992 | Lawes et al. | 623/20 |
| 5,137,536 | 8/1992 | Koshino | 623/20 |
| 5,246,459 | 9/1993 | Elias | 623/20 |

OTHER PUBLICATIONS

Smith & Nephew Richards GENESIS™ Total Knee System Catalog (Sep. 1992).

*Primary Examiner*—Michael Powell Buiz
*Assistant Examiner*—Mark S. Leonardo
*Attorney, Agent, or Firm*—Pravel, Hewitt, Kimball & Krieger

[57] ABSTRACT

A method of preparing a patient's proximal tibia with a surgical saw and cutting instrumentation is disclosed. The method of the present invention prepares the patient's proximal tibial to receive a tibial implant. The patient's intramedullary canal is first reamed and then an intramedullary rod is placed in the intramedullary canal as a reference. A first cutting instrument is bound on the rod above the patient's proximal tibia. The first cutting instrument includes a stylus that is used to set the depth of cut by referencing the top of the proximal tibia. The proximal tibia is then transversely cut with the saw by tracking the first cutting guide surfaces with the saw. The first cutting instrument is removed together with its stylus. A secondary cutting instrument is then placed on the rod above the proximal tibia. The second cutting instrument has a cutter at its center for cutting longitudinally into the proximal tibia. A secondary cut is made on the proximal tibia by tracking the secondary cutting instrument and a guide surface provided on the upper end of the cutters that engage the center of the proximal tibia.

9 Claims, 7 Drawing Sheets

TIBIAL RESECTION INSTRUMENTATION AND SURGICAL METHOD

BACKGROUND OF THE INVENTION

1. Field of the Invention

The present invention relates to orthopedic surgical instruments and surgical methods and more particularly relates to an improved method and apparatus for resecting the patient's proximal tibia for installing a knee prosthesis. Even more particularly, the present invention relates to an improved method and apparatus for resecting a patient's proximal tibia using a preliminary cutting guide and then secondarily cutting the proximal tibia with a secondary cutting guide that has blades that penetrate the proximal tibia, the blades having upper guide surfaces thereon that guide a sawblade during cutting.

2. General Background

In knee joint replacement surgery, a surgeon typically affixes two prosthesis components to the patient's femur and tibia. These replacement components are typically known as the femoral component and the tibial component.

The femoral component is placed on a patient's distal femur after the surgeon makes a plurality of surgical cuts. One common type of femoral prothesis has a J-shape. A femoral prosthesis is usually metallic, having a highly polished outer femoral articulating surface.

A common type of tibial prosthesis uses a laterally extending tray that is shaped to conform to the patient's proximal tibia after the proximal tibia has been cut transversely by the surgeon. The tibia prosthesis also includes a stem or plug that extends generally perpendicular to the tray and from the center of the tray. The stem is placed in a surgically formed opening that extends into the patient's intramedullary canal from the transverse cut formed on the proximal tibia.

A plastic, polymeric insert is attached to the tibial tray. This insert provides a tibial articulating surface that articulates with the femoral articulating surface as the patient's tibia moves through a full range of motion with respect to the patient's femur.

One of the problems with knee joint replacement surgery is that of accurately fitting the patient. Each patient has a different bone structure and geometry. Even though the surgeon uses x-rays to study a particular patient's anatomy at the knee, the surgeon does not have a perfect appreciation of the patient's anatomy until after the knee has been surgically exposed and the surgeon begins to make cuts on the femur and the tibia.

Knee prosthetic components are not available in infinite sizes. The surgeon must examine the patient's anatomy, make the requisite surgical cuts and install prosthesis components that fit.

A number of tibial components have been patented that relate to tibial components having a tray, a plastic insert with articulating surface, and a stem portion that provides initial fixation when the prosthesis is implanted. Other patents have issued that relate to cutting instrumentation for preparing the patient's proximal tibia to receive a tibial prosthetic insert as part of knee joint replacement surgery.

The Murray U.S. Pat. No. 4,016,606 discloses a knee prosthesis that includes a tibial component with a tray and with a stem adapted to be received in a longitudinal bore in the patient's femur. The stem has one end that is integral with a depending generally spheroidal surface having generally the same radius as the radius of the spheroidal depression in the insert.

In the Chiarizzio U.S. Pat. No. 4,601,289 there is disclosed a femoral trial prothesis/rasp assembly used in hip implant surgery. The assembly includes a handle that grips the combination trial prothesis/rasp in a secure manner by clamping over and locking on to a post on the trial prothesis/rasp which later serves as a mounting piece for a femoral prothesis head used in trial reductions.

A modular tibial prosthesis is disclosed in the Shaw U.S. Pat. No. 4,938,769. The Shaw patent discloses a tibial prosthesis for use during a total knee arthroplasty procedure which includes a modular two part tibial component comprising an in-bone anchorage assembly to which is removably attached a tibial tray adapted to receive and retain a bearing insert. Removal of the tray permits access to the interface between the bone and anchorage assembly in the event removal or revision are necessary. In preferred embodiments, the invention affords hybrid fixation of the tibial prosthesis in that bone cement for immediate fixation and adaptation for longer term bone ingrowth are featured. Shaw also discusses the use of porous coatings to enhance fixation.

U.S. Pat. No. 4,938,769 issued to James Shaw discloses an end bone anchorage assembly for a tibial prosthesis that includes an axially elongated central stem and a plurality of elongated fixation pegs spaced from the stem. The stem and the pegs have proximal and distal ends. The proximal ends of the stem define an attachment table. A plurality of structural links interconnect the pegs and the stem. Means is provided for removably attaching a tibial tray to the assembly wherein each of the pegs is connected to the stem by the structural link.

A tibial component for a replacement knee prosthesis is disclosed in the Lawes et al. U.S. Pat. No. 5,080,675. Lawes discloses a tibial component for a replacement knee prosthesis comprising a tibial tray for connection to a suitably prepared tibia, the tray carrying fixed lateral and medial condylar bearing components. Only the medial component has a shock absorber located beneath it.

U.S. Pat. No. 5,137,536 issued to Tomihisa Koshino describes a tibial component for an artificial knee joint. The tibial component includes a plate section having an upper surface and a pair of bearing surfaces parts that are adapted to be in sliding contact with a femoral component. A stem portion extends downwardly from a lower surface of the plate section. A pair of blade like members extend obliquely and posteriorly from the stem. The plate section has a lower surface with a plurality of elongated grooves for improving affinity with respect to the surrounding bone, the grooves including a first group of grooves and a second set of group of grooves extending perpendicularly to the first group of grooves.

An example of a modular tibial support is seen in the Elias U.S. Pat. No. 5,246,459 entitled "Modular Tibial Support Pegs for the Tibial Component of a Prosthetic Knee Replacement System". The Elias Patent discloses a modular tibial support peg operable to secure a tibial component of a knee joint prothesis to a tibia having a groove. The modular tibial support peg includes a cylindrical body with a ridged outer surface operable to engage the groove in the tibia. The modular tibial support peg further includes a plurality of spikes extending inferiorly from the cylindrical body. The spikes are operable to engage the tibia at the inferior end of the groove.

SUMMARY OF THE INVENTION

The present invention provides an improved method of preparing a patient's proximal tibia with a surgical saw. The method of the present invention uses cutting instrumentation for guiding the saw when shaping the patient's proximal tibia with cuts to receive a tibial implant.

The patient's tibial intramedullary canal is first drilled to receive an intramedullary rod. The surgeon then places the rod in the intramedullary canal and mounts cutting guide instruments to that rod as part of the method of the present invention.

A first cutting instrument is mounted on the rod above the patient's proximal tibia. The first cutting instrument has transverse cutting guide surfaces for guiding a surgical saw during an initial cutting of the proximal tibia. The first cutting instrument also provides a stylus with an adjustable stylus member that can reference the proximal tibia before cutting begins. The surgeon then sets a selected depth of cut with the stylus and engages the proximal tibial surface with the stylus.

After the depth of cut has been set using the stylus, the proximal tibia is cut with a first transverse cut. During this first cut, the saw tracks the cutting guide surfaces and then engages the proximal tibial bone tissue. The first cutting instrument and its stylus are then removed.

A second cutting instrument is then mounted on the rod above the patient's proximal tibia. The second cutting instrument has guide surfaces externally of the proximal tibia for guiding a surgical saw blade and a cutter thereon that includes multiple blades for cutting longitudinally into the proximal tibia. After the secondary cutting instrument is mounted into position, a secondary transverse cut is made on the proximal tibia using the secondary cutting instrument. The saw first tracks the guide surfaces externally of the proximal tibia and then tracks a cutting guide surface on the blades.

In the preferred method of the present invention, the primary and secondary cuts are made generally perpendicular to the rod and thus to the patient's intramedullary canal.

With the method of the present invention, the cutter on the secondary cutting instrument includes a plurality of flat blades that are thrust completely into the patient's proximal tibial bone tissue. The blades are imbedded in the proximal tibia. The top surface of the cutter blades is slightly below the surface of the first transverse cut. This allows the surgeon to use the secondary cutting instrument to track not only the secondary cutting instruments externally of the tibia but also to track a guide surface provided on the upper surface of the cutter blades that have been imbedded in the patient's proximal tibial bone tissue.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
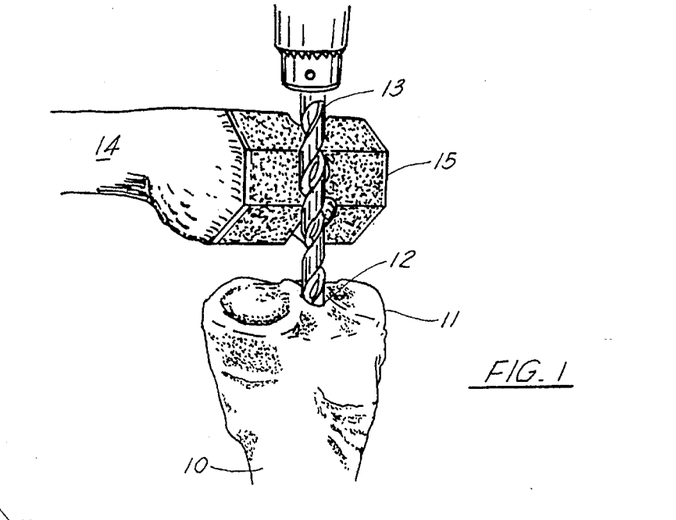
FIG. 1 is a perspective schematic view illustrating preliminary tibial preparation.

FIGS. 1–4 illustrate a preliminary preparation of the patient's distal tibia as part of the method of the present invention. In FIG. 1, the patient's tibia 10 is shown as is the proximal tibia 11. A drill 13 is used to track the patient's intramedullary canal 12 for receiving a reamer 21. Also shown in FIG. 1 is the patient's femur 14 that has already been surgically prepared to receive a trial femoral prosthesis. The distal femur 15 is typically prepared with anterior and posterior cuts that are parallel to each other, a distal cut that is generally perpendicular to the anterior and posterior cuts, and diagonally extending chamfer cuts that extend between the distal cut and the respective posterior and anterior cuts.

Figure 2:
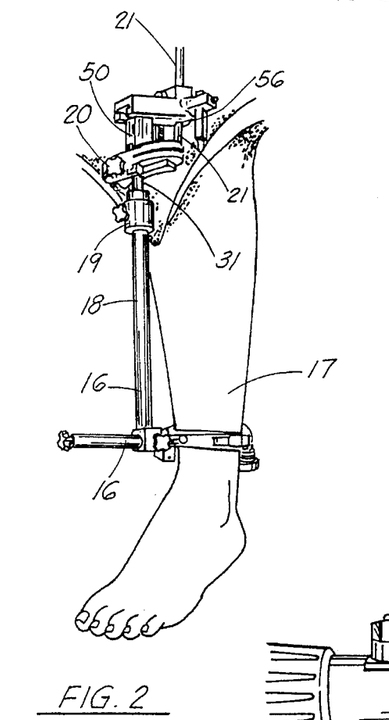
FIG. 2 is a schematic perspective view illustrating attachment of an ankle clamp and the preferred embodiment of the apparatus of the present invention illustrating the tibial cutting block and tibial stylus portions thereof.

In FIG. 2, an ankle clamp 16 has been installed at the patient's ankle 17 and with an alignment sleeve 18 that is positioned generally parallel to the patient's tibia. The sleeve 18 provides a coupling 19 for forming a connection with the bottom of tibial cutting guide 20 of the present invention. Ankle clamps 16 are commercially available and can be seen for example in the Steele U.S. Pat. No. 5,197,944, incorporated herein by reference.

Figure 3:
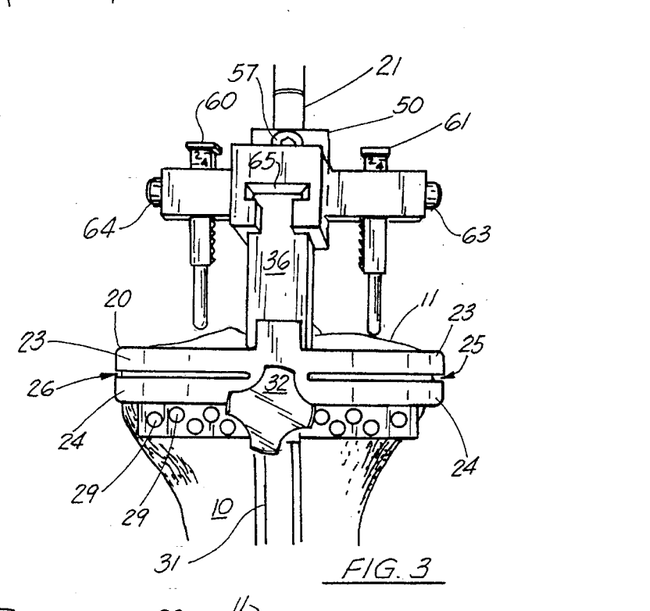
FIG. 3 is a perspective view illustrating the tibial cutting block and the tibial stylus portion of the preferred embodiment of the apparatus of the present invention.
Figure 5:
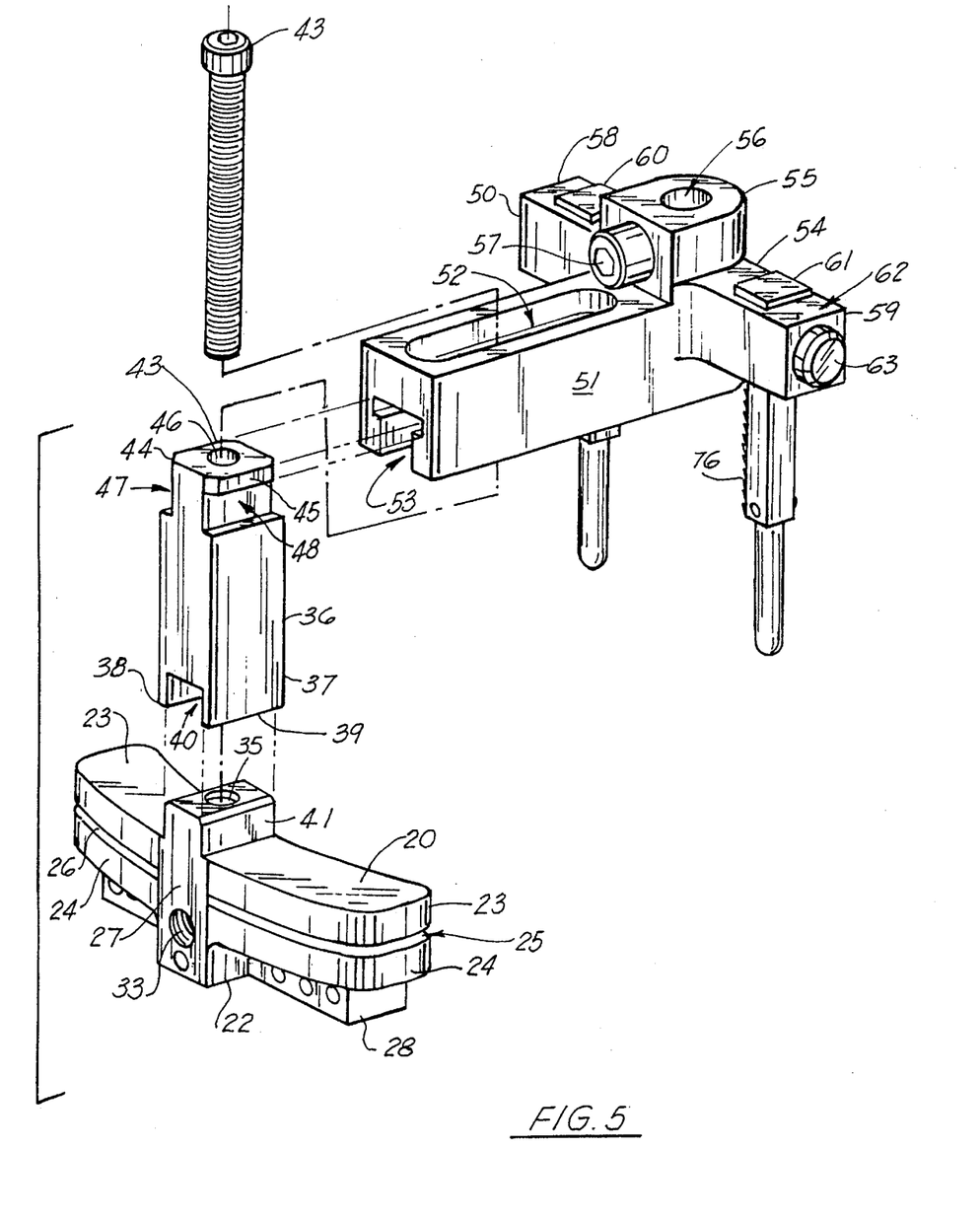
FIG. 5 is a perspective exploded view illustrating the tibial cutting block and the tibial stylus portion of the preferred embodiment of the apparatus of the present invention.
Figure 6:
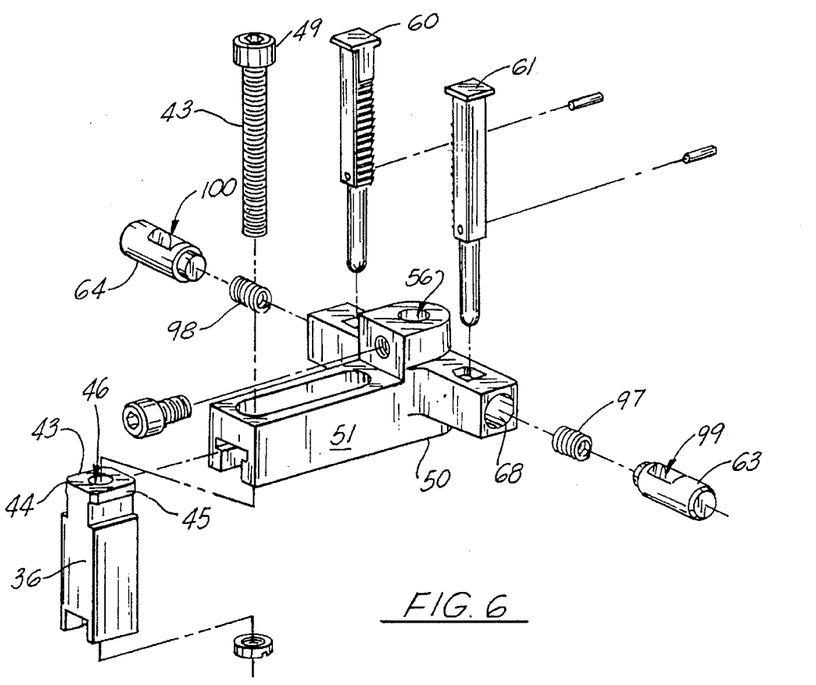
FIG. 6 is an exploded perspective view illustrating the tibial stylus.
Figure 6A:
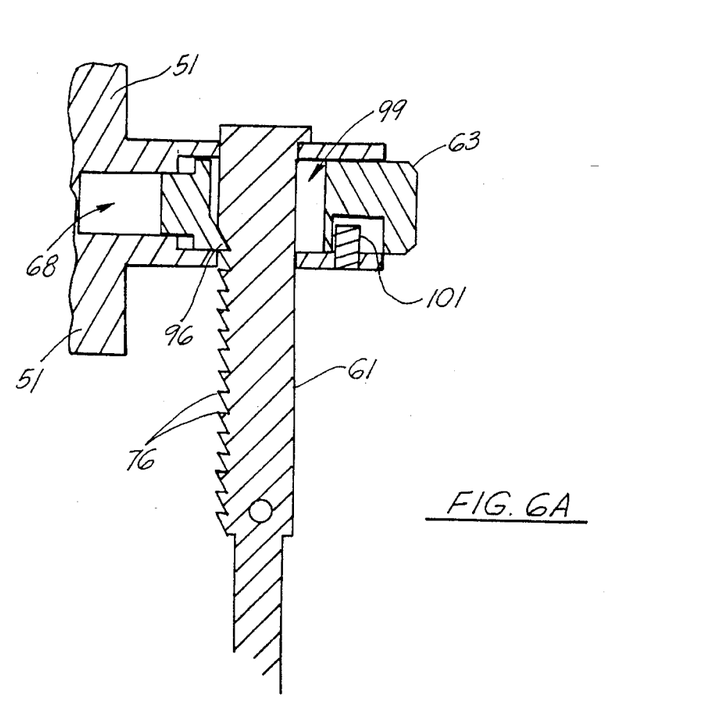
FIG. 6A is a sectional elevational fragmentary view illustrating the tibial stylus.
Figure 7:
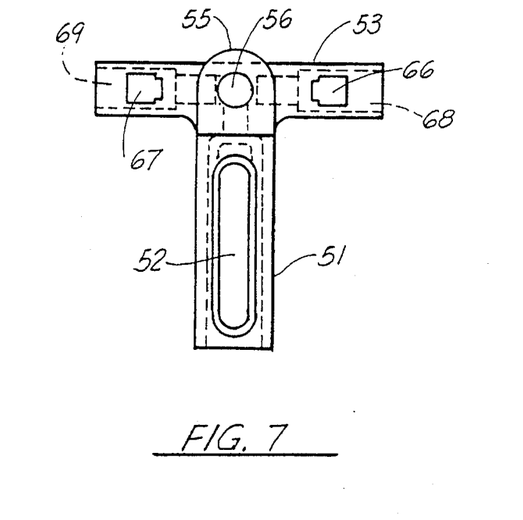
FIG. 7 is a top view illustrating the tibial stylus portion of the preferred embodiment of the apparatus of the present invention.
Figure 8:
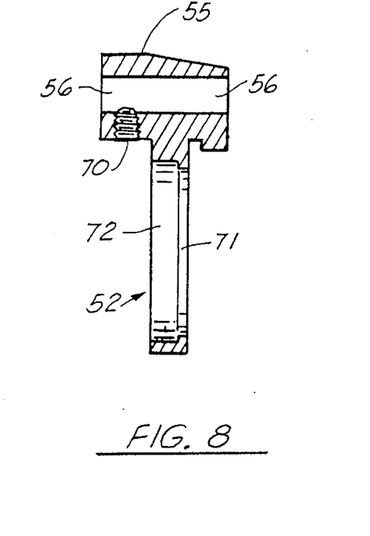
FIG. 8 is partial sectional view illustrating the tibial stylus.
Figure 9:
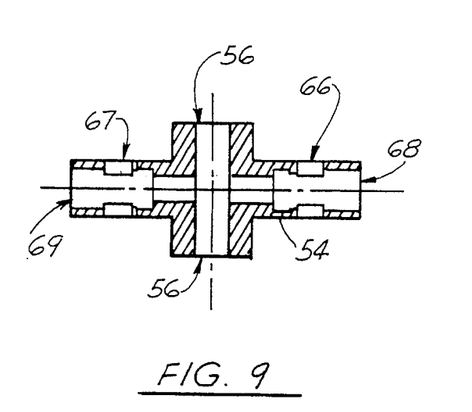
FIG. 9 is partial perspective view of the tibial stylus.
Figure 10:
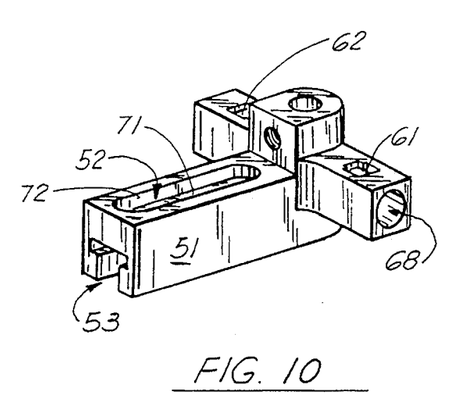
FIG. 10 is a fragmentary view of the tibial stylus.
Figure 11:
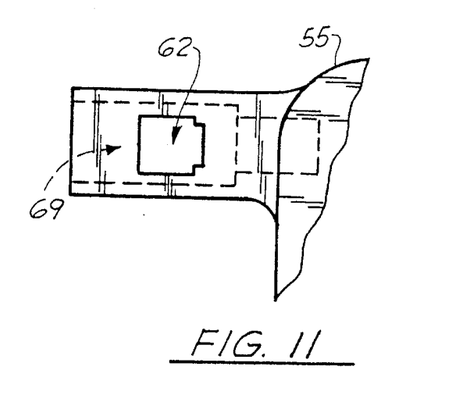
FIG. 11 is another fragmentary sectional view of the tibial stylus.
Figure 12:
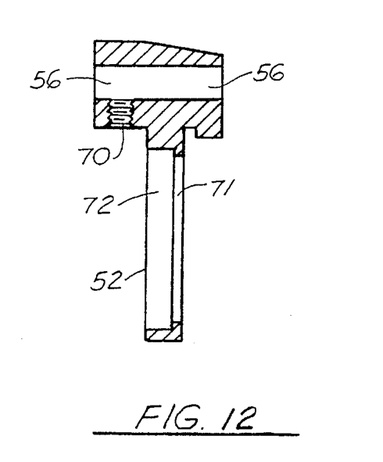
FIG. 12 is a fragmentary sectional view of the preferred embodiment of the apparatus of the present invention.

In FIG. 3, the tibial cutting guide 20 can be seen placed adjacent the patient's proximal tibia 11. In FIGS. 3 and 5–6, the tibial cutting guide 20 can be seen attached to the tibial stylus 50, and the assembly of cutting guide 20 and stylus 50 being attached to reamer 21 mounted in the patient's intramedullary canal. Stylus 50 is shown more particularly in FIGS. 5–12. Cutting block 20 is shown more particularly in FIGS. 13–16.

Figure 4:
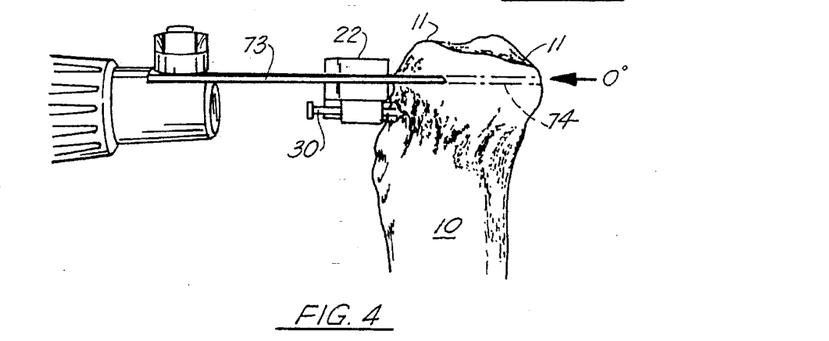
FIG. 4 is a fragmentary perspective view illustrating a cutting of the proximal tibial using the tibial cutting block.

Cutting block 20 includes a block body 22 that includes a pair of upper flanges 23 and a pair of lower flanges 24. Slots 25, 26 extend between the upper flanges 23 and the lower flanges 24. The slots 25, 26 provide a guide for a flat cutting blade such as the cutting blade 73 shown in FIG. 4 which can be a commercially available powered saw. The saw blade 73 cuts through the patient's proximal tibia 11 as shown in FIG. 4 along a line 74 that is generally perpendicular to the patient's intramedullary canal. In FIG. 4, the block 22 has been attached to the proximal tibia 11 using a plurality of bone spikes 30.

Figure 13:
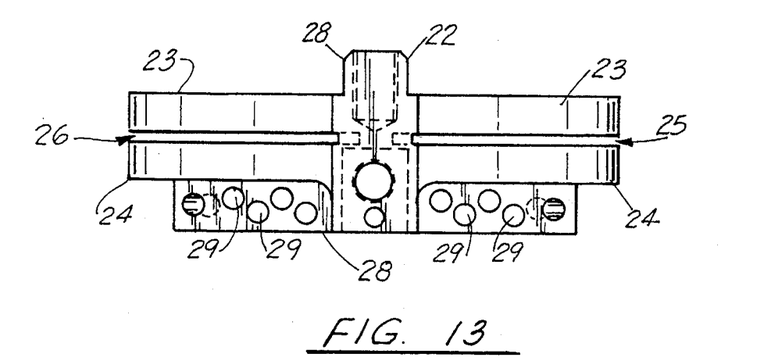
FIG. 13 is a front elevational view of the tibial cutting block portion of the preferred embodiment of the apparatus of the present invention.
Figure 14:
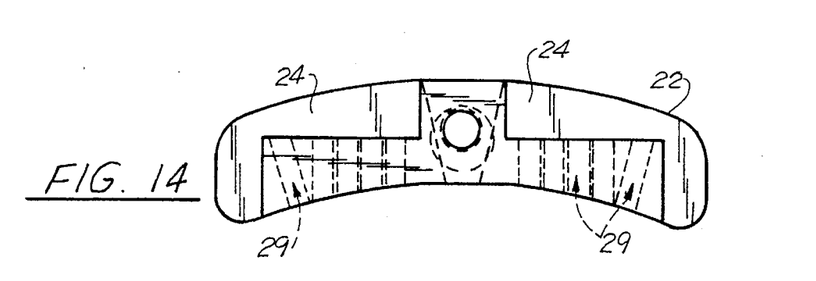
FIG. 14 is a top view of the tibial cutting block of the preferred embodiment of the apparatus of the present invention.
Figure 15:
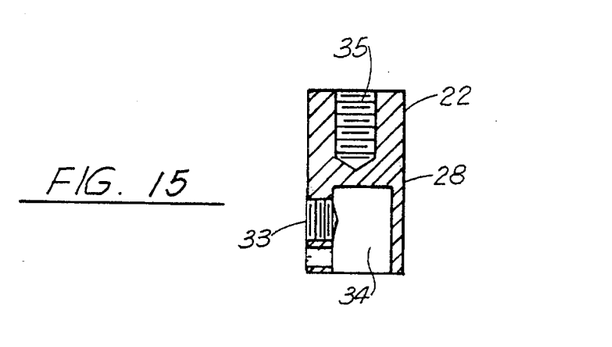
FIG. 15 is a sectional view of the tibial cutting block of the preferred embodiment of the apparatus of the present invention.
Figure 16:
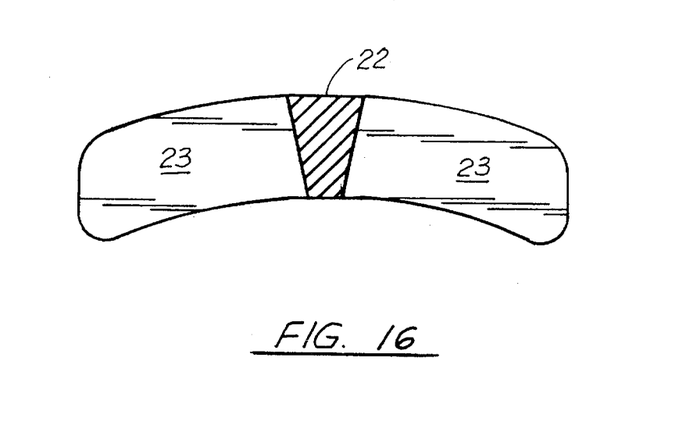
FIG. 16 is a partial sectional view of the tibial cutting block of the preferred embodiment of the apparatus of the present invention.

Tibial cutting block 22 further provides a center portion 22 that can be used to attach the cutting block 22 to the tibial stylus 50 and to ankle clamp 16 at coupling 19. Cutting block body 22 provides a lower attachment portion 28 having a plurality of cylindrical bores 29 therethrough as shown in FIGS. 13 and 14. These cylindrical openings 29 provide a cylindrical shape that corresponds generally to the outer configuration of a bone spike 30. One or more bone spikes can be placed through a corresponding plurality of the openings 29 for affixing the block 22 to the patient's proximal tibia after alignment has been accomplished using elongated reamer rod 21 placed in the patient's intramedullary canal, the stylus 50, and ankle clamp 16.

Vertical rod 31 extends from coupling 19 to center portion 27 of tibial cutting block 22. A set screw 32 threadably engages opening 33 of central portion 28 of cutting block 22. Cylindrical socket 34 receives the upper end of vertical rod 31. The set screw 32 can be tightened against the rod as it occupies the cylindrical socket 34.

An upper cylindrically-shaped internally threaded opening 35 allows the cutting block 22 to be attached to tibial stylus 50. Vertical post 36 extends between stylus 50 and cutting block 22. The post 36 has a central longitudinal axis that is perpendicular to the plane defined by slots 25, 26. Further, the central longitudinal axis of post 36 is parallel to the central longitudinal axis of reamer rod 21 that is mounted in the patient's intramedullary canal. The post 36 has a lower end 37 with a pair of flanges 38, 39 having a recess 40 therebetween.

An upwardly projecting portion 41 of the center portion 8 of cutting block 22 registers in the recess 40. Further, the flanges 38, 39 closely conform to the projecting portion 41 upon assembly. A threaded connection can be used to form a connection between the threaded opening 35 and bolt 49 that extends through vertical bore 46 of vertical post 36. A bolted connection can be used to assemble the vertical post 36 to the cutting block 22, for example.

A pair of shoulders 44, 45 at the upper end of vertical post 36 register in an elongated slot 53 on tibial stylus 50. The upper end 43 of post 36 has a transverse cross section that corresponds in size and shape to the transverse cross section of the longitudinally extending slot 53. Slot 53 extends through horizontal beam 51 or tibial stylus 50. The slot 53 communicates with a longitudinal opening 52 in the upper surface of the horizontal beam 51. A transverse probe holder 54 extends at generally right angles to the beam 51. A bushing 55 extends upwardly from the connection between beam 51 and probe holder 54. The bushing 55 provides a vertical open ended bore 56 that receives reamer 21. Set screw 57 can be used to tighten bushing 55 and the entire tibial stylus 50 to reamer 21. Internally threaded opening 70 receives the set screw 57.

Probe holder 54 includes a pair of sides 58, 59 each having an elongated vertically extending probes 60, 61 respectively. The probe holder 54 has an upper generally flat surface 62 that is perpendicular to the central longitudinal axis of bore 56 and to the central longitudinal axis reamer rod 21. Each probe 60, 61 moves vertically in an opening 66, 67 respectively. A pair of horizontal openings 68, 69 carry detent locking members 63, 64 respectively. The detent locking members 63, 64 can be spring loaded with sprpings 97, 98. Each of the detent locking members 63, 64 have openings that allow the probes 60, 61 to pass therethrough. Each probe 60, 61 provides a plurality of vertically spaced teeth 76 thereon (see FIG. 6). Spaces between the teeth 76 are engaged by the respective detent locking member 63, 64 at stop 96 when they are released, thereby affixing the position of each of the probes 60, 61 relative to the probe holder 54. A stop pin 101 holds each detent locking member 63, 64 in its opening 68, 69.

Longitudinal opening 52 is surrounded by side walls 72 and by longitudinally extending shoulders 71. This allows the placement of a bolt 49 into slot 52 and through the center of vertical bore 46 of vertical post 36 for attaching to threaded opening 35. Further, the head 43 of the bolt 49 rests on the shoulder 71 transferring load thereto.

In FIGS. 17–18 and 21–23, there can be seen tibial secondary prep guide 75. Guide 75 has an instrument body 76 that includes a pair of spaced apart vertical posts including the post 77 and the post 82. Post 77 carries a cylindrical cutting element 78 with a plurality of circumferentially spaced and radially extending cutting blades 79–81. The post 82 supports a pair of flanged portions including upper flanges 83 and lower flanges 84.

Figures 21, 22:
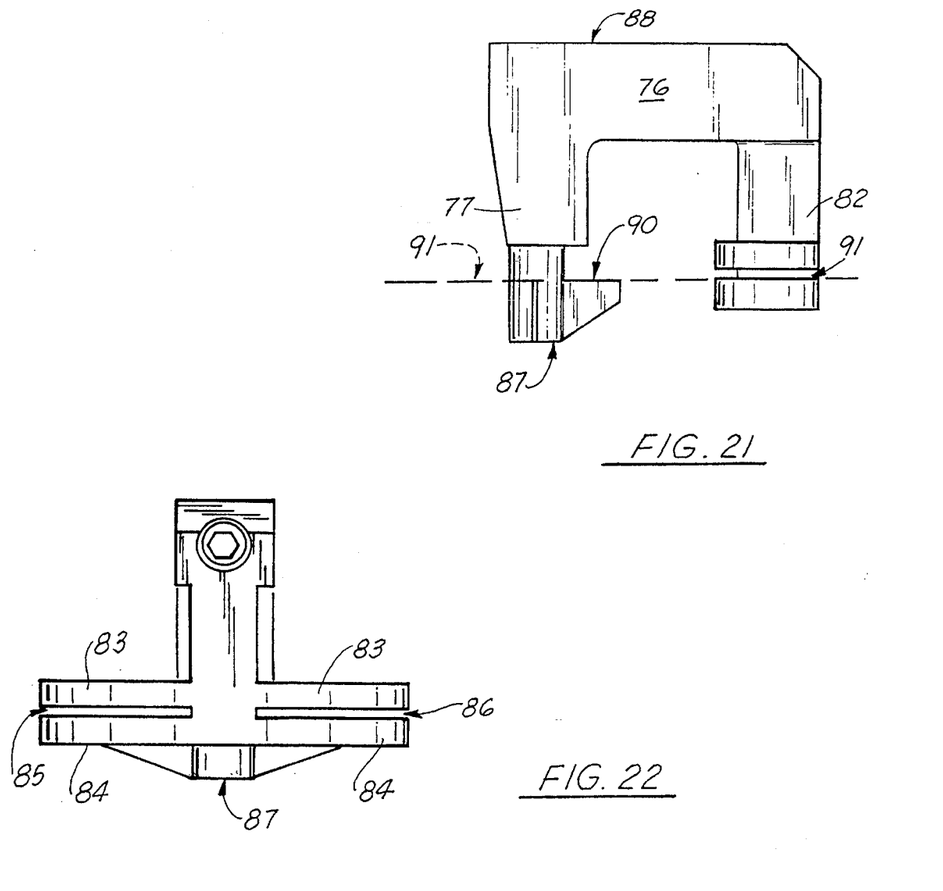
FIG. 21 is a perspective view of the tibial secondary prep-guide portion of the preferred embodiment of the apparatus of the present invention.
FIG. 22 is a frontal elevational view of the tibial secondary prep-guide.
Figure 23:
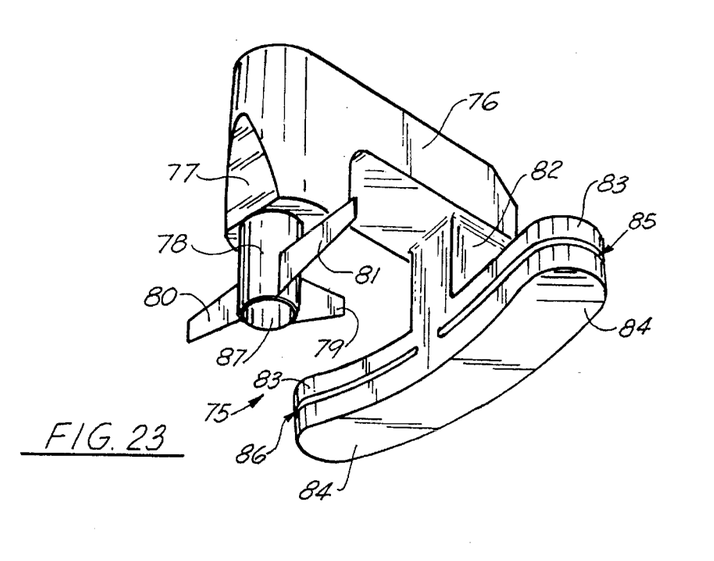
FIG. 23 is an elevational side view of the tibial prep-guide.

A pair of flat cutting blade guide slots 85, 86 are positioned between the upper flanges and the lower flanges 84, as shown in FIGS. 21–23. During use, the surgeon places the tibial secondary prep guide over the reamer 21 that is installed in the patient's intramedullary canal. This registers the three cutting blades 79–81 and the cylindrical cutting element 78 at the center of the patient's proximal tibia 11, as shown in FIG. 17.

Figure 17:
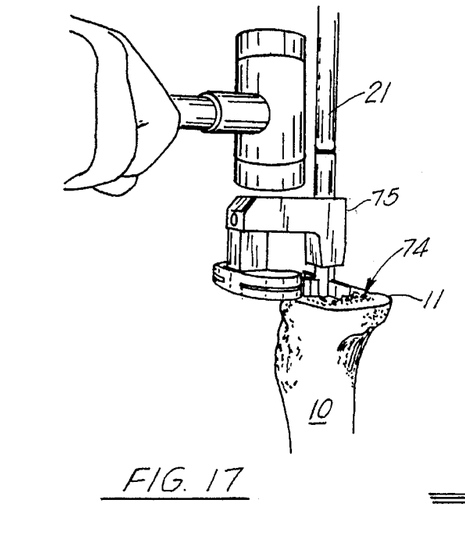
FIG. 17 is a perspective view illustrating placement of the tibial secondary prep-guide portion of the preferred embodiment of the apparatus of the present invention.
Figure 18:
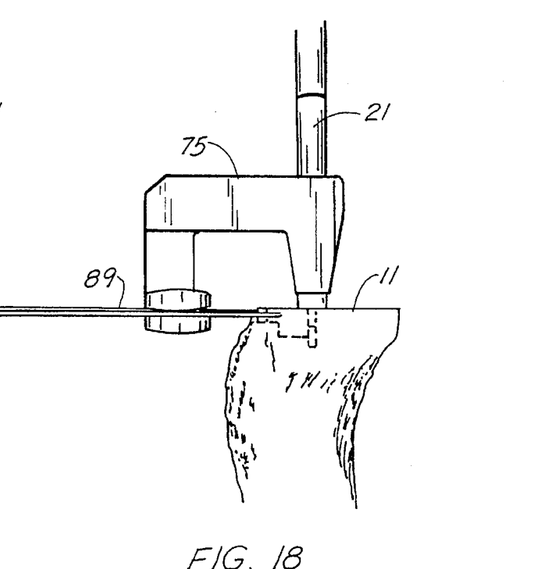
FIG. 18 is a perspective view illustrating the tibial secondary prep-guide and a secondary finishing of the proximal tibia.

The surgeon hammers the flat side 88 of instrument body 76 driving the cutting blades 79–81 into the proximal tibia 11 as shown in FIGS. 17–18. The surgeon hammers the surface 88 until the blades 79–81 are just beneath the surface of proximal tibia 11 as shown in FIG. 18. This allows the surgeon to shave a layer of tissue from proximal tibia 11 with great precision. The saw blade 89 is supported not only by the flanges 83, 84, but also by the upper surfaces 90 of blades 79–81 which are in a common plane with the upper surface 91 of the flange 84, as shown in FIG. 31. The dotted line 102 in FIG. 21 shows the path taken by saw blade 89 to secondarily cut the proximal tibia.

Figure 19:
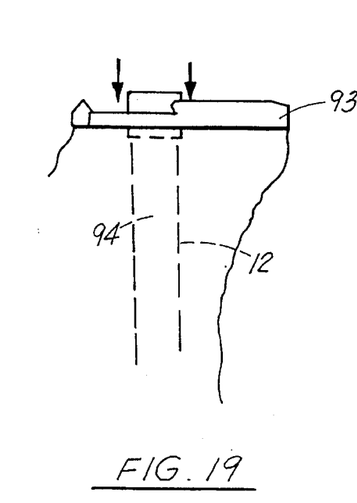
FIG. 19 illustrates installation of a trial tibial prosthesis in the patient's proximal tibia.
Figure 20:
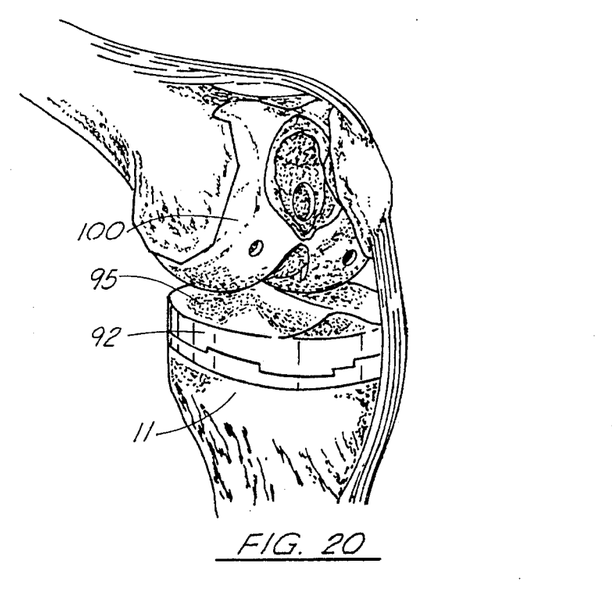
FIG. 20 illustrates the trial femoral prosthesis and the trial tibial prosthesis installed respectively on the patient's distal femur and proximal tibia and prior to rotation to the tibial trial prosthesis.

After the secondary cut is made to the proximal tibia 11, a trial prosthesis can be installed on the patient's distal tibia 11. In FIGS. 19–20, a tibial trial prosthesis 92 is shown as installed into the patient's intramedullary canal 12. The tibial trial prosthesis 92 can include three components, a metallic plate or tray 93, a stem or plug 94, and a plastic trial insert 95. In FIG. 20, a tibial prosthesis 92 has been installed by the surgeon on the patient's proximal tibial 11. The surgeon has also installed a trial femoral prosthesis 100 on the distal femur 15.

The following table lists the parts numbers and parts descriptions as used herein and in the drawings attached hereto.

PARTS LIST

| Part Number | Description |
| --- | --- |
| 10 | tibia |
| 11 | proximal tibia |
| 12 | intramedullary canal |
| 13 | drill |
| 14 | femur |
| 15 | distal femur |
| 16 | ankle clamp |
| 17 | ankle |
| 18 | alignment sleeve |
| 19 | coupling |
| 20 | tibial cutting guide |
| 21 | elongated reamer rod |
| 22 | cutting block body |
| 23 | upper flange |
| 24 | lower flange |
| 25 | horizontal slot |
| 26 | horizontal slot |
| 27 | center portion |
| 28 | attachment portion |
| 29 | cylindrical bores |
| 30 | bone spikes |
| 31 | vertical rod |
| 32 | set screw |
| 33 | internally threaded opening |
| 34 | cylindrical socket |
| 35 | internally threaded opening |
| 36 | vertical post |
| 37 | lower end |
| 38 | flange |
| 39 | flange |
| 40 | recess |
| 41 | projecting portion |
| 43 | head |
| 44 | shoulder |
| 45 | shoulder |
| 46 | vertical bore |
| 47 | recess |
| 48 | recess |
| 49 | bolt |
| 50 | tibial stylus |
| 51 | horizontal beam |
| 52 | longitudinal opening |
| 53 | longitudinal opening |
| 54 | probe holder |
| 55 | bushing |
| 56 | vertical open ended bore |
| 57 | set screw |
| 58 | side |
| 59 | side |
| 60 | probe |
| 61 | probe |
| 62 | flat surface |
| 63 | detent locking member |
| 64 | detent locking member |
| 65 | bolted connection |
| 66 | opening |
| 67 | opening |
| 68 | horizontal opening |
| 69 | horizontal opening |
| 70 | internally threaded opening |

PARTS LIST

| Part Number | Description |
| --- | --- |
| 71 | longitudinally extending shoulder |
| 72 | side wall |
| 73 | saw blade |
| 74 | transverse cut |
| 75 | tibial secondary prep guide |
| 76 | body |
| 77 | vertical post |
| 78 | cylindrical cutting element |
| 79 | blade |
| so | blade |
| 81 | blade |
| 82 | vertical post |
| 83 | upper horizontal flange |
| 84 | lower horizontal flange |
| 85 | cutting guide slot |
| 86 | cutting guide slot |
| 87 | open ended vertical bore |
| 88 | flat surface |
| 89 | blade |
| 90 | upper surface |
| 91 | upper surface |
| 92 | trial prosthesis |
| 93 | tray |
| 94 | stem |
| 95 | insert |
| 96 | stop |
| 97 | spring |
| 98 | spring |
| 99 | opening |
| 100 | opening |
| 101 | stop pin |
| 102 | transverse cutting plane |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of preparing a patient's proximal tibia with a surgical saw and cutting instrumentation to receive a tibial implant comprising the steps of:

a) reaming the patient's tibial intramedullary canal;

b) placing a referencing member in the intramedullary canal;

c) attaching a primary cutting instrument on the referencing member near the patient's proximal tibia, the primary cutting instrument having transverse cutting guide surfaces for guiding the saw during a cutting of the proximal tibia and a stylus with an adjustable stylus member that can reference the proximal tibia before cutting begins;

d) setting a depth of cut with the stylus;

e) engaging the proximal tibial surface with the stylus;

f) cutting the proximal tibia transversely with the saw by tracking the cutting guide surfaces with the saw;

g) removing the first cutting instrument and its stylus;

h) attaching a secondary cutting guide on the referencing member, said secondary cutting guide having a structural support member for cutting longitudinally into the proximal tibia; and i) making a secondary transverse cut on the proximal tibia using the secondary cutting instrument, to more precisely prepare the proximal tibia to receive the tibial implant.

2. The method of claim 1 wherein step "f" comprises forming cuts that are generally perpendicular to the referencing member.

3. The method of claim 1 wherein step "i" includes forming cuts with the blade that are generally perpendicular to the referencing member.

4. The method of claim 1 wherein step "i" includes forming cuts with a structural support member that includes a fin that tracks parallel to the referencing member axis during cutting of the proximal tibia.

5. The method of claim 1 wherein step "i" includes forming cuts into the proximal tibia with a structural support member that includes a plurality of flat fins.

6. The method of claim 1 wherein step "d" includes setting a depth of cut with the stylus by positioning the cutting guide surfaces of the first cutting block a predetermined distance below the lower end of the stylus.

7. The method of claim 1 wherein step "c" comprises mounting a stylus on the referencing member, the stylus having a beam that supports a first cutting block thereon, the cutting instrument having transverse cutting guide surfaces for guiding the saw during a cutting of the proximal tibia, and the first cutting block is adjustable upon the beam into positions that vary in distance from the referencing member.

8. The method of claim 1, wherein step "i" comprises making a secondary cut on the proximal tibia using the second cutting instrument and registering the saw on the secondary cutter when making the secondary cut.

9. A method of preparing a patient's proximal tibia with a surgical saw and cutting instrumentation to receive a tibial implant comprising the steps of:

a) reaming the patient's tibial intramedullary canal;

b) placing a referencing member in the intramedullary canal;

c) attaching a first cutting instrument on the referencing member, the cutting instrument having transverse cutting guide surfaces for guiding the saw during a cutting of the proximal tibia;

d) cutting the proximal tibia transversely with the saw by tracking the cutting guide surfaces with the saw;

e) removing the first cutting instrument;

f) attaching a second cutting instrument on the referencing member above the patient's proximal tibia, said second cutting instrument having a structural support member cutting into the proximal tibia; and g) making a secondary transverse cut on the proximal tibia using the second cutting instrument, to more precisely prepare the proximal tibia to receive the tibial implant.

* * * * *